United States Patent
Maddox et al.

(10) Patent No.: US 9,040,619 B2
(45) Date of Patent: May 26, 2015

(54) 1,3-DIKETOAMIDE FUNCTIONAL POLYMERS AND COMPOSITIONS EMPLOYING THE SAME

(71) Applicant: Eastman Chemical Company, Kingsport, TN (US)

(72) Inventors: John Thorton Maddox, Jonesborough, TN (US); Stacey James Marsh, Church Hill, TN (US); Garry Kenneth Weakley, Kingsport, TN (US); Peter Webb Raynolds, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 30 days.

(21) Appl. No.: 13/671,919

(22) Filed: Nov. 8, 2012

(65) Prior Publication Data

US 2014/0128537 A1 May 8, 2014

(51) Int. Cl.
| | |
|---|---|
| *C08F 216/14* | (2006.01) |
| *C09D 129/10* | (2006.01) |
| *C07C 231/04* | (2006.01) |
| *C07C 235/80* | (2006.01) |
| *C08F 2/22* | (2006.01) |
| *C08F 2/18* | (2006.01) |
| *C08F 2/04* | (2006.01) |

(52) U.S. Cl.
CPC ......... *C08F 216/1458* (2013.01); *C07C 231/04* (2013.01); *C08F 2/22* (2013.01); *C08F 2/18* (2013.01); *C08F 2/04* (2013.01); *C09D 129/10* (2013.01)

(58) Field of Classification Search
CPC .................. C07C 235/80; C08F 216/1458
See application file for complete search history.

(56) References Cited

U.S. PATENT DOCUMENTS

| | | | |
|---|---|---|---|
| 4,839,413 A | 6/1989 | Kiehlbauch et al. | |
| 4,927,876 A | 5/1990 | Coogan et al. | |
| 4,939,233 A | 7/1990 | Jenkins et al. | |
| 4,946,932 A | 8/1990 | Jenkins | |
| 5,137,961 A | 8/1992 | Goos et al. | |
| 5,247,040 A | 9/1993 | Amick et al. | |
| 5,889,098 A | 3/1999 | Trumbo | |
| 2007/0238827 A1* | 10/2007 | Brady et al. | 524/556 |
| 2011/0160368 A1* | 6/2011 | Bohling et al. | 524/210 |
| 2012/0157609 A1 | 6/2012 | Maddox et al. | |

FOREIGN PATENT DOCUMENTS

EP    1798258 A1 *  6/2007

OTHER PUBLICATIONS

Asua, J. M. Emulsion Polymerization: From Fundamental Mechanisms to Process Developments. Journal of Polymer Science Part A: Polymer Chemistry, vol. 42, pp. 1025-1041. 2004.*
Smith, Oliver W., et al.; "New vinyl ester monomers for emulsion polymers", Progress in Organic Coatings, 22, pp. 19-25, (1993).
PCT International Search Report dated Dec. 17, 2013 for International Application No. PCT/US2013/021804.

* cited by examiner

*Primary Examiner* — Robert C Boyle
*Assistant Examiner* — Stephen Rieth
(74) *Attorney, Agent, or Firm* — Dennis V. Carmen

(57) ABSTRACT

A 1,3-diketoamide functional monomer represented by the following formula (1):

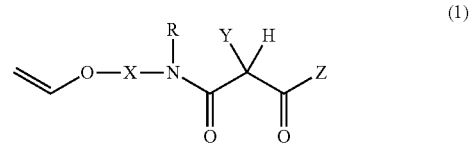

(1)

wherein R and Y are independently selected from the group consisting of hydrogen, an alkyl group having from 1 to 10 carbon atoms, an aryl group having from 6 to 20 carbon atoms, and an aralkyl group having from 7 to 20 carbon atoms; and wherein X and Z are independently selected from the group consisting of an alkyl group having from 1 to 10 carbon atoms, an aryl group having from 6 to 20 carbon atoms, and an aralkyl group having from 7 to 20 carbon atoms. Also disclosed are emulsion, suspension, and solution polymers comprising residues from the 1,3-diketoamide functional monomer of formula 1 and, optionally, one or more additional ethylenically unsaturated monomers. Both latex and self-curing coating compositions described herein exhibit excellent hydrolytic stability, including increased retention of 1,3-diketo functionality.

33 Claims, No Drawings

1,3-DIKETOAMIDE FUNCTIONAL POLYMERS AND COMPOSITIONS EMPLOYING THE SAME

FIELD OF THE INVENTION

This invention relates to ethylenically unsaturated, 1,3-diketoamide functional polymers and compositions produced therefrom. In particular, this invention relates to polymers having a 1,3-diketoamide functionality and the use of these polymers in various compositions.

BACKGROUND

In light of increasingly stringent regulations, reduction of volatile organic compounds (VOC) emissions from paint and other coatings has become a key concern of the coatings industry. Powder or solid coatings, water-based systems, and low solvent/high solids formulations have each been utilized as potential low-VOC alternatives, but each of these systems also has practical performance and economic drawbacks. For example, powder coating emits nearly no VOCs, but, as its application requires heating the substrate, such systems cannot necessarily be universally applied. Water-based systems, such as latexes, have also been used as low VOC coatings, but typically require the presence of a relatively high VOC solvent in order to provide a final coating exhibiting acceptable chemical and thermal resistance. In addition, most low solvent/high solids coating formulations require use of low molecular weight polymeric materials and, consequently, must be cross-linked via application of heat or UV light in order to achieve an acceptable finish. As such post-treatments are not always feasible, such coatings have limited application.

To remedy this problem, a few "self-curing" coatings have been developed that utilize an auto-oxidizing polymer, such as those containing the monomer Acetoacetoxyethyl methacrylate (AAEM), which cross-links in the absence of any additional treatment. Unfortunately, AAEM-based coatings are hydrolytically labile and may degrade under hydrolyzing conditions. Such degradation can be minimized with addition of one or more additives, such as ammonia, but the presence of these additives often adversely impacts the color and/or odor of the final coating.

Thus, a need exists for a hydrolytically stable polymer suitable for use in a low VOC, self-curing coating composition. Desirably, the polymer and coatings produced therefrom would be economically viable and could easily be implemented on a large production scale for a minimal cost.

SUMMARY

One embodiment of the present invention concerns a process for producing a polymer. The process comprises subjecting at least one 1,3-diketoamide functional monomer having a vinyl ether group, or precursors thereto, to polymerization to thereby provide a polymer comprising 1,3-diketoamide functional moieties.

Another embodiment of the present invention concerns a composition comprising (a) a polymer comprising 1,3-diketoamide functional moieties; (b) at least one 1,3-diketoamide functional monomer comprising a vinyl ether group; and (c) an evaporable liquid carrier.

Yet another embodiment of the present invention concerns a 1,3-diketoamide functional polymer comprising residues of at least one monomer represented by the formula (1):

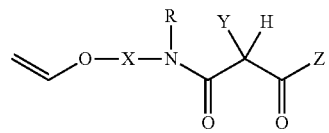

wherein R and Y are independently selected from the group consisting of hydrogen, an alkyl group having from 1 to 10 carbon atoms, an aryl group having from 6 to 20 carbon atoms, and an aralkyl group having from 7 to 20 carbon atoms; and wherein X and Z are independently selected from the group consisting of an alkyl group having from 1 to 10 carbon atoms, an aryl group having from 6 to 20 carbon atoms, and an aralkyl group having from 7 to 20 carbon atoms.

DETAILED DESCRIPTION

According to one embodiment of the present invention a 1,3-diketoamide functional monomer is provided. Polymers including residues of such a monomer, either alone or in combination with one or more ethylenically unsaturated copolymers, can be useful in or as a coating composition, such as, for example, an auto-oxidizable or "self-curing" coating composition. In contrast to other conventionally-prepared coatings, compositions formulated according to embodiments of the present invention exhibit enhanced hydrolytic stability over time and thermal variation, while still producing a final coating that retains sufficient hardness and chemical and block resistance. Additional features and benefits of may become apparent as several embodiments of the present invention are described in detail below.

In accordance with one embodiment, there is provided a 1,3-diketoamide functional monomer, useful for preparing a coating composition, that comprises, consists essentially of, or consists of a 1,3-diketoamide group and a vinyl ether group. The monomer may be represented by the following formula (1):

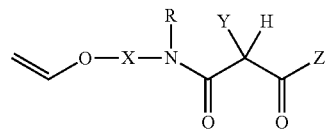

wherein R and Y are independently selected from the group consisting of hydrogen, an alkyl having from 1 to 10 carbon atoms, an aryl having from 6 to 20 carbon atoms, and an aralkyl having from 7 to 20 carbon atoms; and wherein X and Z are independently selected from the group consisting of an alkyl having from 1 to 10 carbon atoms, an aryl having from 6 to 20 carbon atoms, and an aralkyl having from 7 to 20 carbon atoms. It should be understood that the ranges provided herein are intended to be inclusive and to encompass the end point values given, as well as the values within the range. The alkyl groups may be unsaturated or saturated and can be branched, cyclic, or unbranched (straight chain). The aryl and aralkyl groups may also be saturated or unsaturated and may also be configured to include branched, cyclic, or unbranched (straight chain) portions.

In another embodiment, R is hydrogen, Y is hydrogen or an alkyl having between 1 and 10 carbon atoms, and X and Z are each independently an alkyl having between 1 and 10 carbon atoms. In still further embodiments, R and Y are hydrogen and X and Z are independently alkyls having between 1 and 5 carbon atoms, and in another embodiment, R and Y are hydrogen, X is propyl, and Z is methyl. The monomer may be, for example, 3-oxo-N-(3-(vinyloxy)propyl)butanamide.

The monomers described above can be prepared using one or more suitable methods. For example, in one embodiment, a diketene-delivering reagent, such as, for example, diketene, t-butyl acetoacetate, or the diketene-acetone adduct TKD, may be reacted with an amine to form a first reaction product. In some embodiments, the first reaction product may comprise an intermediate, such as 3-oxobutanamide; while, in other embodiments, the final 1,3-diketoamide functional monomer may be recovered directly from the first reaction product. According to one embodiment, the 1,3-diketoamide functional monomer described herein may be prepared by reacting the diketene delivering reagent with an amine to install the 3-oxobutanamide moiety followed by reaction with a vinyloxy reagent to install the vinyl ether moiety. Alternatively, the ethylenically unsaturated 1,3-diketoamide functional monomer may be prepared by reacting a suitable vinyloxy amine with the diketene delivering reagent to install the 3-oxobutanamide moiety.

The resulting 1,3-diketoamide functional monomers are capable of being addition polymerized, alone or with one or more copolymerizable monomers, to produce a homopolymer or copolymer having 1,3-diketoamide functionality. In one embodiment, the 1,3-diketoamide functional polymer may be derived from the monomers described herein and can include residues of the 1,3-diketoamide functional monomer represented by formula (1) above. Such residues may comprise 1,3-diketoamide pendant groups, reacted such that at least a portion of the monomer remains as a pendant moiety. Typically, the monomer can be reacted into the polymer via the ethylenic unsaturation of the vinyl ether group and, accordingly, the final polymer may or may not itself include vinyl ether moieties. However, at least a portion of the 1,3-diketoamide monomer described herein does remain and, as such, the polymers of the present invention can comprise residues of the monomers represented by formula (1) above.

In one embodiment, the 1,3-diketoamide functional polymer of the present invention can be a copolymer and may further comprise residues of at least one copolymerizable monomer. Suitable copolymerizable monomers can include, but are not limited to, one or more ethylenically unsaturated comonomers, such as, for example, acrylic and methacrylic acid esters, styrenic monomers, and vinyl monomers. Such comonomers may be commercially available or may be produced via known methods.

Suitable acrylic or methacrylic acid esters include those having a $C_1$-$C_{20}$ alcohol moiety. Examples of such esters include, but are not limited to, methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylates, furyl (meth)acrylate, methylfuryl (meth)acrylate, butylfuryl (meth)acrylate, tetrahydrofuryl (meth)acrylate, ethoxyethyl (meth)acrylate, isobornyl (meth)acrylate, hydroxyethyl (meth)acrylate, hydroxypropyl (meth)acrylate, and combinations thereof.

In addition, acrylic and methacrylic acid esters may contain additional functional groups, such as, hydroxyl, amine, halogen, ether, carboxylic acid, amide, nitrile, and alkyl group. Examples of such esters can include, but are not limited to, carbodiimide (meth)acrylate, methyl (meth)acrylate, ethyl (meth)acrylate, butyl (meth)acrylate, isobutyl (meth)acrylate, ethylhexyl (meth)acrylate, octyl (meth)acrylate, isobutyl (meth)acrylate, allyl (meth)acrylate, glycidyl (meth)acrylates, and combinations thereof.

Suitable styrenic monomers can include styrene, as well as substituted styrenes such as $C_1$-$C_6$ alkyl ring-substituted styrene, $C_1$-$C_3$ alkyl alpha-substituted styrene and combinations of ring and alpha-alkyl substituted styrenes. Examples of styrenic monomers can include, but are not limited to, styrene, vinyl toluene, m-methyl styrene, p-methyl styrene, o-methyl styrene, p-butyl styrene, alpha-methyl styrene, and combinations thereof.

Suitable vinyl monomers can include, but are not limited to, vinyl esters, carboxylic-acid functional vinyl monomers, non-acid vinyl monomers, and combinations thereof. The acid-functional vinyl monomers used may be selected broadly from carboxylic acids, phosphonic acids, acid anhydrides, phosphate monomers, and other functionalities which are capable of reacting with a base to form a salt. Examples of suitable carboxylic acid-functional vinyl monomers, include, but are not limited to, acrylic acid, methacrylic acid, itaconic acid, itaconic anhydride, citraconic acid, citraconic anhydride, and maleic anhydride. Suitable vinyl esters can include, for example, vinyl acetate, vinyl propionate, vinyl 2-ethylhexanoate, vinyl neononoate, vinyl neodecanoate, and vinyl esters of versatic acid. Such monomers are described in The Brandon Worldwide Monomer Reference Guide and Sourcebook, Second Edition, 1992, Brandon Associates, Merrimack, N.H.; and in Polymers and Monomers, the 1996-1997 Catalog from Polyscience, Inc., Warrington, Pa. Additionally, vinyl esters can include, for example, vinyl esters of vinyl alcohol such as the VEOVA series, commercially available from Shell Chemical Company as VEOVA 5, VEOVA 9, VEOVA 10, and VEOVA 11 products. See O. W. Smith, M. J. Collins, P. S. Martin, and D. R. Bassett, Prog. Org. Coatings 22, 19 (1993).

The 1,3-diketoamide functional polymers and copolymers described herein can be derived from one or more of the monomers and comonomers described above, or precursors thereto, and may be addition polymers formed via free-radical addition polymerization. In such addition polymers, the propagating species may be a free radical, and the resulting polymer can be formed in a chain-growth fashion polymerization as typically understood in the art. Polymers according to embodiments of the present invention may be formed as solution polymers, as emulsion (or latex) polymers, or as suspension polymers according to any suitable process. In one embodiment, the polymerization can begin with one or more monomers and, optionally, at least one comonomer, while, in another embodiment, the precursors to the monomer and/or comonomer be reacted to form in situ monomers, which can then be polymerized to form a polymer having at least 1,3-diketoamide functional moieties.

Solution Polymerization

During solution polymerization, one or more of the monomers and, optionally, comonomers discussed previously can be polymerized in an inert solvent. In particular, one or more 1,3-diketoamide functional monomers, alone or in combination with one or more comonomers listed above, may be free radical polymerized in a non-reactive solvent to provide a polymers having at least a 1,3-diketoamide functional moiety. The heat produced by the polymerization can be absorbed by the solvent, which can help control the rate of reaction. Typically, solution polymerization can be carried out at a temperature of at least about 35° C., at least about 40° C., at least about 45° C. and/or not more than about 95° C., not more than about 90° C., or not more than about 85° C.

In addition, in some embodiments, solution polymerization may also be carried out in the presence of a free radical initiator (oxidant) and/or a reducing agent, optionally combined with at least one catalyst. Any suitable initiator can be used and is typically present in an amount of at least about 0.05 weight percent, at least about 0.10 weight percent, at least about 0.50 weight percent and/or not more than 6 weight percent, not more than about 3 weight percent, not more than about 2 wt percent, based on the total weight of monomers. Exemplary initiators include water-soluble or water-dispersible free-radical initiators, such as ammonium persulfate, sodium persulfate, hydrogen peroxide, t-butylhydroperoxide, ammonium sulfate, alkali sulfate, di-benzoyl peroxide, lauryl peroxide, di-tertiarybutylperoxide, 2,2'-azobisisobutyronitrile, benzoyl peroxide, and combinations thereof.

In some embodiments, the free-radical initiator may be combined with similar amounts of at least one reducing agent to form a redox initiating system. Such a reducing agent may be any agent capable of increasing the rate of polymerization may include, for example, one or more of sodium bisulfite, sodium hydrosulfide, sodium formaldehyde sulfoxylate, ascorbic acid, isoascorbic acid, and mixtures thereof. Additionally, one or more polymerization catalysts may also be used in order to increase the rate of polymerization by, for example, promoting decomposition of the free radical initiator under the reaction conditions. Suitable catalysts can include, but are not limited to, AQUACAT® catalyst (commercially available from Johnson Matthey, London, England) and other transition metal compounds such as ferrous sulfate heptahydrate, ferrous chloride, cupric sulfate, cupric chloride, cobalt acetate, cobaltous sulfate, and mixtures thereof. When present, the polymerization catalyst can be employed in a similar amount as the free-radical initiator and/or reducing agent.

In one embodiment, one or more chain transfer agents may also be employed during polymerization. Suitable chain transfer agents may include, but are not limited to, butyl mercaptan, n-octylmercaptan, n-dodecyl mercaptan, butyl or methyl mercaptopropionate, mercaptopropionic acid, 2-ethylhexyl 3-mercaptopropionate, n-butyl 3-mercaptopropionate, isodecylmercaptan, octadecylmercaptan, mercaptoacetic acid, haloalkyl compounds, (such as carbon tetrabromide and bromodichloromethane). Several suitable reactive chain transfer agents are also described in U.S. Pat. No. 5,247,040, the disclosure of which is incorporated herein by reference. In particular, mercaptopropionate, allyl mercaptopropionate, allyl mercaptoacetate, crotyl mercaptopropionate and crotyl mercaptoacetate, and mixtures thereof may be utilized in to various embodiments of the present invention.

Suspension and Emulsion Polymerization

According to another embodiment of the present invention, polymers having a 1,3-diketoamide functional moiety may also be prepared via suspension or emulsion polymerization. During emulsion polymerization, an emulsified monomer solution is polymerized in an aqueous medium, typically under agitation, while, suspension polymerization involves polymerizing one or more monomers suspended in a continuous aqueous phase. Both processes may be carried out in the presence of a free-radical initiator and, optionally, a reducing agent, a catalyst, and/or a chain transfer agent of the types and I the amounts described previously. Additionally, suspension and emulsion polymerization processes may be conducted at a reaction temperature within the ranges provided above.

During emulsion or suspension polymerization, one or more surfactants may be used as a stabilizer or an emulsifier. The surfactant may be an anionic or non-ionic surfactant and may be present in an amount of at least about 0.05 weight percent, at least about 0.10 weight percent, at least about 0.15 weight percent and/or not more than about 8 weight percent, not more than about 6 weight percent, or not more than about 4 weight percent, based on the total weight of monomers. Examples of suitable surfactants can include, but are not limited to, alkali or ammonium alkylsulfate, alkylsulfonic acid or fatty acid, oxyethylated alkylphenol, sulfosuccinates and derivatives, or any combination of anionic or non-ionic surfactants. A further list of surfactants is available in the treatise: McCutcheon's Emulsifiers & Detergents, North American Edition and International Edition, MC Publishing Co., Glen Rock, N.J. 1993.

Additionally, in some embodiments of the present invention, one or more copolymerizable monomers or surfactants other than those listed above may also be included during polymerization in order to produce polymers and compositions having desirable end properties. Such additional monomers or surfactants may be included to facilitate particle nucleation and/or growth during polymerization. In the same or other embodiments, one or more of these additives may be added subsequently to enhance the stability of the polymer or to modify one or more of its final properties, including, for example, surface tension or wettability. These additional monomers or surfactants may be added as part of the suspension or latex composition, or may be at least partially copolymerized with the monomers described previously. When utilized, such additional monomers or surfactants can be present in an amount of at least about 2 weight percent, at least about 5 weight percent, at least about 10 weight percent and/or not more than about 30 percent, not more than about 25 weight percent, or not more than about 20 weight percent, based on the total amount of monomer.

In one embodiment, a wet adhesion promoting monomer may be used during polymerization. Examples of suitable wet adhesion promoting monomers include, but are not limited to, monomers such as t-butylaminoethyl methacrylate, dimethylaminoethyl methacrylate, diethylaminoethyl methacrylate, N,N-dimethylaminopropyl methacrylamide, 2-t-butylaminoethyl methacrylate, N,N-dimethylaminoethyl acrylate and N-(2-methacryloyloxy-ethyl) ethylene urea. Additionally, at least one water-dispersible or water-soluble polymer may also be utilized for controlling the formation of the polymer and/or stabilizing the final aqueous composition. Suitable water-dispersible or water-soluble polymers can include water-dispersible polyesters as described in U.S. Pat. Nos. 4,946,932 and 4,939,233; water-dispersible polyurethanes as described in U.S. Pat. Nos. 4,927,876 and 5,137,961; and alkali-soluble acrylic resins as described in U.S. Pat. No. 4,839,413, the disclosures of which are all incorporated herein by reference.

In the same or other embodiments, the polymer can also include at least one polymerizable surfactant, which can be an ethylenically unsaturated copolymerizable surfactant. The copolymerizable surfactant may include an isopropenyl phenyl or allyl groups and/or may comprise polyoxyethylene alkyl phenyl ether moieties. Copolymerizable surfactants may be anionic, such as those comprising sulfate or sulfonate group, or nonionic surfactants. In one embodiment, the polymerizable surfactant may include sodium alkyl allyl sulfosuccinate.

Both suspension and emulsion polymerization result in an aqueous polymeric dispersion, of which the latter type is often referred to as a latex composition. Additional details regarding latex compositions according to embodiments of the present invention will be discussed in detail shortly. Typically, suspension polymers have an average particle size less than the average particle size of an emulsion polymer. For example, in one embodiment, the average particle size of a suspension polymer prepared as described herein can be at least about 2 µm, at least about 3 µm, at least about 4 µm and/or not more than about 25 µm, not more than about 20 µm, or not more than about 15 µm. Emulsion polymers, however, may have a particle size of, for example, at least about 80 nm, at least about 100 nm, at least about 125 nm and/or not more than about 300 nm, not more than about 250 nm, or not more than about 200 nm, measured with a MICROTRAC laser light scattering device. Both emulsion and suspension polymers can have any suitable shape, including, for example, a spherical form, a multi-lobe form, a peanut shell form, an acorn form, or a raspberry form. In some embodiments, suspension and/or emulsion polymers as described herein may also have a core-in-shell or gradient structure.

In one embodiment, the emulsion or suspension polymers described herein may have a weight average molecular weight (Mw) of at least about 1,000, at least about 2,000, at least about 5,000 and/or not more than about 1,000,000, not more than about 500,000, or not more than about 250,000, as determined by gel permeation chromatography (GPC). In some embodiments, the glass transition temperature of these polymers may be at least about 0° C., at least about 15° C., at least about 20° C. and/or no more than about 100° C., not more than about 80° C., not more than about 60° C., or not more than about 50° C., or in the range of from about 0° C. to about 100° C., about 15° C. to about 80° C., or about 20° C. to about 50° C., as measured via differential scanning calorimeter (DSC) under nitrogen at a heating rate of 20° C./min.

Latex and Coating Compositions

According to one embodiment of the present invention, there is provided a latex composition comprising a polymer having at least 1,3-diketoamide functional moieties and an evaporable liquid carrier. Typically, the carrier can be an aqueous carrier and can include less than about 1 weight percent, less than about 0.5 weight percent, or less than about 0.05 weight percent of an organic solvent. In some embodiments, in addition to the polymers and copolymers described herein, the latex composition may also include a relatively small amount of 1,3-diketoamide functional monomer, particularly if such a monomer was used to produce the latex polymer. In one embodiment, residual 1,3-diketoamide functional monomer, represented by formula (1) above, may be present in the latex composition or other polymeric aqueous dispersion in an amount of at least about 0.05 parts per million by weight (ppmw), at least about 1 ppmw, at least about 2 ppmw and/or not more than about 100 ppmw, not more than about 50 ppmw, not more than about 25 ppmw, or not more than 10 ppmw, based on the total weight of the composition.

One or more of the monomers, polymers, and/or latex compositions described herein may be useful in various types of coating compositions. In one embodiment, one or more 1,3-diketoamide functional monomers, alone or in combination with one or more other comonomers, and optionally with a free radical initiator, may be directly applied to a substrate as a coating composition. According to this embodiment, once applied, the monomers may be allowed to in situ polymerize thereby forming a polymeric coating.

Alternatively, a coating composition may be formed by combining one or more solution polymers with an aqueous carrier and optionally including less than about 10 weight percent, less than about 5 weight percent, or less than about 2 weight percent of one or more surfactants. In other embodiments, the coating can include a latex or other aqueous dispersion applied directly to the substrate, optionally combined with additional liquid carrier. In some embodiments, the coating composition may include both polymeric and monomeric constituents, but may comprise less than about 100 ppmw, less than about 50 ppmw, less than about 25 ppmw, or less than 10 ppmw of the monomer, based on the total weight of the composition.

In one embodiment, the coating composition may include one or more additional initiators or agents for cross-linking the polymer and "curing" the applied coating. In another embodiment, the coating composition of the present invention may be a "self-curing" coating composition, such that the composition that is able to build molecular weight before, during, or after drying without an additional thermal or chemical cross-linking agent. In some embodiments, such compositions are able to achieve a gel fraction, as described in Example 4 herein, of at least about 70, at least about 75, at least about 80, at least about 85, at least about 90, or at least about 95 without the addition of heat, UV light, or a chemical cross-linker.

Advantageously, the monomers, polymers, latexes, and/or coating compositions of the present invention can also exhibit excellent hydrolytic stability. As used herein, the term "hydrolytic stability" refers to the ability of the material to resist degradation or decomposition when exposed to hydrolyzing conditions. In one aspect, the hydrolytic stability of a monomer, polymer, or latex can be determined by measuring the ability of the material to retain a desired functionality, such as, for example, a 1,3-diketo functionality, over time and when exposed to certain conditions. According to one embodiment, the polymers, latexes, and coating compositions of the present invention may have a 1,3-diketo functional retention of at least about 70 percent, at least about 75 percent, at least about 80 percent, at least about 85 percent, at least about 90 percent, or at least about 95 percent after 56 days, when tested according to the procedure described in detail in Example 4. Monomers, polymers, and compositions of the present invention are substantially more hydrolytically stable than many conventional polymers and latexes, such as AAEM modified with ammonia, which tends to degrade under similar conditions.

The various aspects of the present invention can be further illustrated and described by the following Examples. It should be understood, however, that these Examples are included merely for purposes of illustration and are not intended to limit the scope of the invention, unless otherwise specifically indicated.

EXAMPLES

Example 1

Preparation of
3-oxo-N-(3-(vinyloxy)propyl)butanamide

A 1-L jacketed flask was charged with 100 grams of diketene (1186 mmol) and 100 grams of 3-(vinyloxy)propan-1-amine (989 mmol) at a rate of 1 gram per minute. The contents of the flask were stirred and the reaction temperature was maintained at or below 30° C. After the addition was complete, the reaction mixture was observed to be a yellow to light orange oil, which was allowed to solidify. The resulting solid 3-oxo-N-(3-(vinyloxy)propyl)butanamide, which weighed approximately 50 grams, was recovered from the oil and was observed to have a light yellow, waxy appearance.

Example 2

Preparation of Several Latex Emulsions

Three different latex emulsions, Inventive Latex A and Comparative Latexes 1 and 2, were prepared according to the following procedure. A 1000-mL resin kettle equipped with a condenser, a nitrogen purge, and a subsurface feed tube was charged with 116 grams of water, 1.4 grams of DOWAFAX 2A1 (45%, 1.1 phm total), 10 grams of 24 nm acrylic latex seed (20% NVM) and 0.5 mL of 2 weight percent iron solution. The nitrogen purge was started and the contents were stirred and heated to a temperature between 60° C. and 65° C. An oxidant feed stream including 54 grams of water and 1 gram of 70% t-butylhydroperoxide and a reductant feed stream including 1.0 grams of sodium isoascorbate, 2.5 grams of DOWFAX 2A1, and 41 grams of water were fed into the reactor. After 5 minutes, a monomer feed stream, comprising 160 grams of several acrylic polymers, was fed into the reactor. The compositions of the individual monomer feed streams used to prepare Inventive Latex A and Comparative Latexes 1 and 2 are summarized in Table 1, below. The oxidant and reductant feed streams were added over a period of 100 minutes and 175 minutes, respectively, and the monomer feed was added over a period of 55 minutes.

TABLE 1

Monomer Feed Stream Compositions for Various Latex Compositions

| Component | Inventive Latex A | Comparative Latex 1 | Comparative Latex 2 |
|---|---|---|---|
| Methylmethacrylate | 43 wt % | 43 wt % | 45 wt % |
| n-butyl acrylate | 50 wt % | 50 wt % | 53 wt % |
| Methacrylic acid | 2 wt % | 2 wt % | 2 wt % |
| Acetoacetoxyethylmethacrylate (AAEM) | — | 5 wt % | — |
| 3-oxo-N-(3-(vinyloxy)propyl)butanamide | 5 wt % | — | — |

After the feed additions were complete, the reactor contents were allowed to react at 60° C. for an hour before being cooled and neutralized to a pH of 7.8 via addition of 14 weight percent ammonium hydroxide. The resulting latexes were filtered through a 100 mesh wire screen to remove any solids or scrap material. The average particle size and solids content of each of Inventive Latex A and Comparative Latexes 1 and 2 are summarized in Table 2, below.

TABLE 2

Properties of Various Latex Compositions

| Composition | Solids Content, wt % | Average Particle Size, nm |
|---|---|---|
| Inventive Latex A | 45.0 | 87.3 |
| Comparative Latex 1 | 42.6 | 96.0 |
| Comparative Latex 2 | 41.0 | 228.0 |

Example 3

Accelerated Hydrolysis Testing of Several Latexes

The hydrolytic stability of Inventive Latex A and Comparative Latex 1 were evaluated by monitoring the decomposition of the 1,3-diketo species of the respective polymer components. The predominant mode of decomposition for 1,3-diketo species is loss of the acetoacetyl group via formation of acetone and carbon dioxide. Thus, the decomposition over time was measured via GC analysis of the acetone present according to the following procedure.

Each of Inventive Latex A and Comparative Latex 1 were divided into two samples. One sample of each latex was not modified and the other was treated with enough ammonia to achieve a final pH between 8 and 8.3. Four bottles containing the samples were placed in an oven and maintained at a temperature of 52° C. The samples were periodically removed and analyzed via GC to determine the weight percent acetone present. Based on the value obtained, the amount of 1,3-diketo functionality was calculated after 14, 28, 42, and 56 days. The results of this analysis are summarized in Table 3, below.

TABLE 3

Results of Accelerated Hydrolysis Testing of Various Latexes

| | 1,3-Diketo Functionality Retained (%) | | | |
|---|---|---|---|---|
| | Inventive Latex A | | Comparative Latex 1 | |
| Time (days) | Untreated | Treated ($NH_3$) | Untreated | Treated ($NH_3$) |
| 0 | 90.9 | 92.1 | 97.4 | 97.7 |
| 14 | 91.2 | 91.5 | 80.6 | 91.2 |
| 28 | 94.3 | 93.8 | 71.6 | 86.1 |
| 42 | 90.8 | 92.1 | 64.8 | 83.9 |
| 56 | 94.5 | 92.1 | 61.2 | 74.7 |

Comparison of the ammonia-treated Comparative Latex 1 to its untreated counterpart illustrates that the addition of ammonia to AAEM-based latexes slows loss of 1,3-diketo functionality, but does not eliminate it. Further, as shown in Table 3, both the treated and untreated Inventive Latex A experienced very little 1,3-diketo functionality loss, indicating its higher level of inherent hydrolytic stability, as compared to conventionally prepared AAEM-based latexes.

Example 4

Film Gel Fraction of Various Latex Compositions

Film gel fraction was obtained by determining the insoluble weight fraction of polymer in a dry film sample using acetone as solvent. A piece of the dried latex film was cut, placed in a cone formed from a 4"×4" fine mesh steel screen, weighed and then completely immersed in acetone solvent overnight. After this, the screen containing the insoluble residual film was removed, allowed to dry, and then weighed. Dividing the weight of the insoluble residual film by the weight of the original film sample provides the Film Gel Fraction.

Film gel fraction tests, as described above, were performed to evaluate the relative cross-linking ability of Inventive Latex A, Comparative Latex 1, and Comparative Latex 2. Films having a wet thickness of 3 mils of each latex were drawn onto a glass slide and allowed to air dry at room temperature. The resulting slides were placed in a Q-Panel Co. UV light box, which included 6 UVA-340 light bulbs located approximately 5 inches from each sample. After seven days, the samples were removed and analyzed and the results are summarized in Table 4, below.

TABLE 4

Results of Film Gel Fraction Test for Various Latex Compositions

| Latex Composition | Gel Fraction (%) |
|---|---|
| Inventive Latex A | 90 |
| Comparative Latex 1 | 86 |
| Comparative Latex 2 | 25 |

As shown in Table 4, Inventive Latex A and Comparative Latex 1, which includes AAEM functionality, show similar levels of cross-linking. As expected, Comparative Latex 2, which includes no AAEM functionality, has a substantially lower level of cross-linking than either of the other two samples.

The preferred forms of the invention described above are to be used as illustration only, and should not be used in a limiting sense to interpret the scope of the present invention. Obvious modifications to the exemplary one embodiment, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

The invention claimed is:

1. A process for producing a polymer, said process comprising: subjecting at least one 1,3-diketoamide functional monomer to polymerization to thereby provide a polymer comprising 1,3-diketoamide functional moieties, wherein said 1,3-diketoamide functional monomer is represented by the following formula (1):

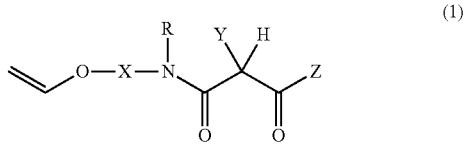

(1)

wherein R and Y are independently selected from the group consisting of hydrogen, an alkyl group having from 1 to 10 carbon atoms, an aryl group having from 6 to 20 carbon atoms, and an aralkyl group having from 7 to 20 carbon atoms, and X and Z are independently selected from the group consisting of an alkyl group having from 1 to 10 carbon atoms, an aryl group having from 6 to 20 carbon atoms, and an aralkyl group having from 7 to 20 carbon atoms.

2. The process of claim 1, wherein R is hydrogen, Y is hydrogen or an alkyl group having from 1 to 10 carbon atoms, and X and Z are each independently an alkyl group having from 1 to 10 carbon atoms.

3. The process of claim 1, wherein R and Y are hydrogen and X and Z are independently alkyl groups having from 1 to 5 carbon atoms.

4. The process of claim 1, wherein R and Y are hydrogen, X is a propyl group, and Z is a methyl group.

5. The process of claim 1, wherein said polymer is a homopolymer comprising 1,3-diketoamide functional moieties.

6. The process of claim 1, further comprising copolymerizing said 1,3-diketoamide functional monomer with at least one comonomer to provide said polymer, wherein said comonomer is selected from the group consisting of methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate, isobutyl (meth)acrylate, styrene, p-methyl styrene, o-methyl styrene, p-butyl styrene, alpha-methyl styrene, and combinations thereof.

7. The process of claim 1, wherein said process is an emulsion polymerization process and said polymer is an emulsion polymer.

8. The process of claim 1, wherein said process is a solution polymerization process and said polymer is a solution polymer.

9. The process of claim 1, wherein said process is a suspension polymerization process and said polymer is a suspension polymer.

10. The process of claim 1, wherein said polymer has a 1,3-diketo functional retention of at least 70 percent.

11. The process of claim 1, wherein the polymerization reaction is started with said 1,3-diketoamide functional monomers.

12. The process of claim 1, wherein said 1,3-diketoamide functional monomers are formed in situ during the polymerization by reacting precursors to the 1,3-diketoamide functional monomer to form said 1,3-diketoamide functional monomer.

13. A latex composition comprising said polymer produced according to the process of claim 1 and an aqueous carrier.

14. A self-curing coating composition comprising said polymer produced according to claim 1.

15. A composition comprising:
(a) a polymer comprising 1,3-diketoamide functional moieties;
(b) at least one 1,3-diketoamide-functional monomer represented by the following formula (1):

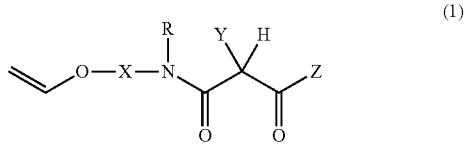

(1)

wherein R and Y are independently selected from the group consisting of hydrogen, an alkyl group having from 1 to 10 carbon atoms, an aryl group having from 6 to 20 carbon atoms, and an aralkyl group having from 7 to 20 carbon atoms; and wherein X and Z are independently selected from the group consisting of an alkyl group having from 1 to 10 carbon atoms, an aryl group having from 6 to 20 carbon atoms, and an aralkyl group having from 7 to 20 carbon atoms; and (c) an evaporable liquid carrier.

16. The composition of claim 15, wherein said 1,3-diketoamide functional monomer is present in said composition in an amount of at least 0.5 ppm, based on the total weight of said composition.

17. The composition of claim 16, wherein said 1,3-diketoamide functional monomer is present in said composition in an amount less than 100 ppm, based on the total weight of said composition.

18. The composition of claim 15, wherein R is hydrogen, wherein Y is hydrogen or an alkyl group having from 1 to 10 carbon atoms, and X and Z are each independently an alkyl group having from 1 to 10 carbon atoms.

19. The composition of claim 15, wherein R and Y are hydrogen, X is a propyl group, and Z is a methyl group.

20. The composition of claim 15, wherein said 1,3-diketoamide functional moieties of said polymer comprise residues of said 1,3-diketoamide functional monomer represented by formula (1).

21. The composition of claim 15, wherein said polymer further comprises residues of one or more comonomers selected from the group consisting of methyl (meth)acrylate, ethyl (meth)acrylate, propyl (meth)acrylate, isopropyl (meth)acrylate, butyl (meth)acrylate, isobutyl (meth)acrylate, hexyl (meth)acrylate, isooctyl (meth)acrylate, isodecyl (meth)acrylate, lauryl (meth)acrylate, stearyl (meth)acrylate, phenoxyethyl (meth)acrylate, methoxyethyl (meth)acrylate, benzyl (meth)acrylate, ethoxyethyl (meth)acrylate, 2-ethylhexyl (meth)acrylate, cyclopentyl (meth)acrylate, isobutyl (meth)acrylate, styrene, p-methyl styrene, o-methyl styrene, p-butyl styrene, alpha-methyl styrene, and combinations thereof.

22. The composition of claim 15, wherein said polymer is an emulsion polymer and said evaporable liquid carrier is an aqueous carrier.

23. The composition of claim 15, wherein said composition has a 1,3-diketo functional retention of at least 70 percent.

24. The composition of claim 15, wherein said composition is a self-curing coating composition having a gel fraction of at least 70.

25. The composition of claim 20, wherein said 1,3-diketoamide functional monomer is present in said composition in an amount of at least 0.5 ppm, based on the total weight of said composition.

26. The composition of claim 25, wherein said 1,3-diketoamide functional monomer is present in said composition in an amount less than 100 ppm, based on the total weight of said composition.

27. A 1,3-diketoamide functional polymer comprising residues of at least one monomer represented by the formula (1):

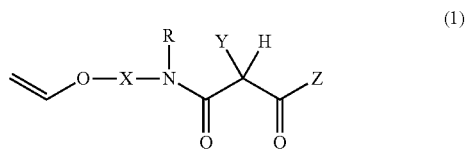

(1)

wherein R and Y are independently selected from the group consisting of hydrogen, an alkyl group having from 1 to 10 carbon atoms, an aryl group having from 6 to 20 carbon atoms, and an aralkyl group having from 7 to 20 carbon atoms; and wherein X and Z are independently selected from the group consisting of an alkyl group having from 1 to 10 carbon atoms, an aryl group having from 6 to 20 carbon atoms, and an aralkyl group having from 7 to 20 carbon atoms.

28. The polymer of claim 27, wherein R is hydrogen, wherein Y is selected from the group consisting of hydrogen and an alkyl group having from 1 to 10 carbon atoms, and X and Z are each independently an alkyl group having from 1 to 10 carbon atoms.

29. The polymer of claim 27, wherein R and Y are hydrogen, wherein X and Z are independently alkyl groups having from 1 to 5 carbon atoms.

30. The polymer of claim 27, wherein R and Y are hydrogen, X is a propyl group, and Z is a methyl group.

31. The polymer of claim 27, wherein said polymer is an emulsion polymer.

32. A latex composition comprising the polymer of claim 27, wherein said latex composition further comprises an evaporable liquid carrier.

33. A self-curing coating composition comprising the polymer of claim 27.

* * * * *